(12) United States Patent
Dutton (10) Patent No.: US 6,368,305 B1
(45) Date of Patent: Apr. 9, 2002

(54) SYRINGE PLUNGER IMMOBILIZING DEVICE

(76) Inventor: Virginia R. Dutton, 307 E. 91st St., New York, NY (US) 10128

( * ) Notice: Subject to any disclaimer, the term of this patent is extended or adjusted under 35 U.S.C. 154(b) by 0 days.

(21) Appl. No.: 09/406,371

(22) Filed: Sep. 28, 1999

Related U.S. Application Data (60) Provisional application No. 60/136,829, filed on Jun. 1, 1999.

(51) Int. Cl.[7] .............................................. A61M 5/32
(52) U.S. Cl. ...................................... 604/192; 604/218
(58) Field of Search ................................ 604/218, 192, 604/198, 110, 263, 117, 197, 241; 606/1, 108

(56) References Cited

U.S. PATENT DOCUMENTS 5,925,032 A * 7/1999 Clements ........................ 606/1

* cited by examiner

Primary Examiner—Manuel Mendez (57) ABSTRACT

A disposable syringe plunger immobilizing device includes first and second hollow members, a means for connecting the first and second hollow members to one another, and a means for holding the first and second hollow members in contact with one another. When in contact with one another, the first and second hollow members contact a syringe plunger and the main body of the syringe to hold the syringe plunger in place in a bore of the main body of the syringe, so that movement of the syringe plunger relative to the main body of the syringe is inhibited. In this fashion, the syringe may be preloaded with a medicament and then safely transported without loss of the medicament within the syringe until the syringe is used. The disposable syringe plunger immobilizing device may be manufactured in different sizes to accommodate various syringe sizes and volumes of medicament to be injected and colors to assist in identification of the various sizes of the device. After use, the disposable syringe plunger immobilizing device may be discarded.

15 Claims, 5 Drawing Sheets

SYRINGE PLUNGER IMMOBILIZING DEVICE

The present application claims priority to U.S. Provisional Patent Application Ser. No. 60/136,829, filed on Jun. 1, 1999.

FIELD OF THE INVENTION

This invention relates generally to the field of disposable and nondisposable medical syringes. More specifically, the present invention relates to a means for preventing movement of a disposable syringe plunger element relative to the body of the syringe, whereby the syringe may be pre-loaded with a fluid medicament to a required dosage level, and thereafter conveniently carried in a pocket or handbag without the necessity of carrying a complete medicament injection kit. While the invention is useful in a wide variety of applications, it is particularly suitable for use in conjunction with the administration of medicaments for diabetes, blood thinning, growth hormones, veterinary injections, and the like.

BACKGROUND OF THE INVENTION

Many drugs used to alleviate the symptoms of a number of diseases or medical conditions require frequent injections. The most widely known example of such a disease is diabetes, although also included in this category are diseases and conditions such as juvenile growth hormone deficiency, migraine headaches, arthritis, penile dysfunction, and certain severe allergic reactions. Often these therapeutics are proteins or other molecules, which are not amenable to oral administration.

Diabetes is a disease wherein the body is unable to regulate the transport of glucose from the bloodstream into the cells of the body for use as a cellular fuel. As a result, diabetics often have too much glucose in their blood. The resulting buildup of glucose in the bloodstream can lead to serious health problems, including heart disease, blindness, kidney failure, and lower extremity amputations. It is estimated that about 16 million people in the United States alone suffer from diabetes, which means that one in 20 persons has the disease. About 385,000 people in the United States die each year from the disease, making it the sixth leading cause of death by disease and the seventh leading cause of death overall. The economic cost of diabetes is staggering—the American Diabetes Association estimates that the health cost of diabetes runs between $92 billion and $138 billion annually. One study predicts that the incidence of diabetes worldwide will increase from the current 2.1% to over 3% by the year 2010, resulting in an estimated total of 220 million cases worldwide.

There are several different types of diabetes. Type 1 diabetes results when the pancreas either does not make insulin, or the body destroys the insulin that is made. In Type 2 diabetes, the pancreas makes sufficient amounts of insulin, but the cells cannot use the insulin. Type 1 diabetes is also called "insulin-dependent diabetes mellitus", because persons with this type of diabetes require insulin shots. Type 1 diabetes is relatively rare, occurring in less than 10% of persons with diabetes. Type 2 diabetes is termed "non-insulin-dependent diabetes mellitus", because at least initially, the persons with this type of disease do not require insulin shots. However, as many as 40% of the persons with Type 2 diabetes will require insulin shots as their disease progresses. Type 2 is by far the most common form of diabetes. Over 90% of persons with diabetes have Type 2 diabetes. Other types of diabetes may develop as a result of pregnancy, specific genetic syndromes, surgery, drugs, malnutrition, infections, and other illnesses. These cases account for 1–2% of all diagnosed cases of diabetes.

Diabetes is defined as a medical condition characterized by fasting plasma glucose levels greater than or equal to 126 mg/dl of blood plasma. Diabetics must monitor their blood glucose levels on a regular basis. To maintain their blood glucose within normal bounds, diabetics must combine careful attention to diet, regular exercise, and frequent injections of insulin. If their blood glucose is outside the normal levels, diabetics may experience disabling complications.

Diabetics must carry their own supplies for insulin injections with them when they are not at their home or other location where they can safely store their supplies. These supplies include one or more syringes, sterile swabs, and liquid supplies of insulin. The supplies are either carried loose, or in a kit which includes a casing element. When required, the syringes are removed and loaded with insulin for injection, and the dose is administered. The supplies are relatively bulky and inconvenient, and their use often requires finding a relatively private location having a surface upon which to place the supplies during use. Furthermore, the user must retain at least a portion of the supplies even after the required dose has been injected.

Insulin pens are often used in place of syringes. These devices are prefilled with an insulin cartridge to inject a required dose. The pens are filled with a certain number of doses, and may or may not be ultimately disposable. The pens do not require the user to carry a bulky vial of insulin. However, the pens are not immediately disposable, and like the kit described above must be carried with the user even after the required dose has been injected. The pens are also more expensive than syringes, and the insulin for use with the pens more expensive than the insulin used with syringes. Furthermore, the pens are bulkier than individual syringes. Since needles and insulin cartridges made specifically for the insulin pens must also be purchased and carried by the user, the pens do not solve the problems of having to carry supplies.

Also available are preloaded syringes, from companies such as Vetter Pharma-Turm. However, these syringes are prefilled by the manufacturer, not the user, and the user is not able to adjust the volume of liquid in the syringe without breaking the seal. Furthermore, these devices are locked with a cap on the needle end of the syringe, which means that no needle may be attached to the syringe prior to transport. The needle must be attached to the syringe after the cap is removed, adding an additional step and supplies to the process.

Other references disclose devices and methods for encasing a syringe for safe transport. U.S. Pat. No. 5,519,931 (Reich) discloses a complex device for transporting a syringe filled with a radioactive material. The device includes a sharps container for holding the syringe and a radiopharmaceutical "pig" for holding the sharps container. U.S. Pat. No. 4,886,497 (Scholl, Jr.) discloses a container for transporting hypodermic syringes. The container includes a first sealed position for ensuring that the container has not been tampered with before use of the syringe, and a second position for sealing the syringe after use for transport and disposal of the used syringe. U.S. Pat. No. 4,634,428 (Cuu) teaches a cover for a disposable syringe that allows rotation of the needle after use for rendering the syringe unusable. U.S. Pat. No. 3,937,219 (Karakashian) and U.S. Pat. No.

3,207,302 (Hobbs) disclose methods of packaging syringes prior to use. These methods are typically awkward and not suitable for use with individual syringes.

In addition, much effort has been focused on developing syringes that avoid the problems of accidental needle sticks and illicit re-use of syringes. For example, U.S. Pat. No. 5,891,092 (Castellano) discloses a disposable syringe that provides a slideable protective cover and a disabling member. After an injection is made using the syringe, the disabling member breaks the sealing, diaphragm of the plunger rod, so that the syringe is rendered incapable of delivering another injection. The slideable protective cover also slides forward to cover the needle and prevent accidental needle sticks. U.S. Pat. No. 5,183,466 (Movern) discloses a hypodermic syringe having a plunger assembly that enables the syringe to be used in a conventional manner but not reused. The syringe barrel contains a plunger lock that engages the plunger piston after filling the syringe with a liquid and allows discharge of the liquid, but thereafter locks the plunger in place and prevents refilling of the syringe. U.S. Pat. No. 4,915,692 (Verlier) describes a non-reusable syringe that accomplishes the same end as Movern. U.S. Pat. No. 3,890,971 (Leeson et al.) discloses a safety syringe that incorporates both a plunger lock and a lockable needle cover to render the syringe incapable of reuse. U.S. Pat. No. 5,506,015 (Fredericksen et al.) discloses a tamper-evident closure seal for syringes that provides an improved method for removing the seal from a release liner without sacrificing the ability of the seal to either adhere strongly to the syringe or to show evidence of tampering with the seal. However, these syringes do not address the problem of how to transport preloaded medicament syringes without the need for a bulky apparatus or retaining anything associated with the injection after use.

In view of the popularity of the disposable syringes, there is a great need for a convenient device that would allow the user to prefill syringes with a desired volume and after use, discard the used syringe without the need to retain anything associated with the injection. The present invention fulfills this need.

SUMMARY OF THE INVENTION

The present invention provides a small, simple device for locking a syringe plunger in place along a syringe barrel. When in place, the device enables a preloaded syringe to be carried anywhere and used immediately, without the need to load the syringe or carry vials of the desired medicine. Furthermore, after use the syringe may be simply discarded, as any other used syringe. Multiple syringes may be loaded in this fashion and carried, relieving the user of the need to carry medicament vials or bulky supplies with them. When used for insulin injections, the present invention also enables the patient to use the less expensive insulin vials, as opposed to the more expensive vials associated with the use of insulin pens. Finally, the present invention allows the user to transport premixed insulins that are not available to the users of insulin pens. As a result, greater flexibility is afforded the patient by the use of the present invention.

Accordingly, it is an object of the present invention to provide a syringe plunger immobilizing device, comprising a first hollow member, a second hollow member, a means for hingeably connecting the first hollow member to the second hollow member, and a means for holding the first hollow member in contact with the second hollow member. More particularly, it is an object of the present invention to provide a syringe plunger immobilizing device, comprising a first hollow member and a second hollow member, each of the hollow members having a main wall, a first side wall, a second side wall, an outer end wall, a frusto-conical inner end wall and a cylindrical sleeve portion. The cylindrical sleeve portion contacts the inner end wall. The first side wall is connected to the main wall along a first edge of the main wall, and the second side wall is connected to the main wall along a second edge substantially parallel to the first edge such that the first side wall is opposite the second side wall. The outer end wall is connected to the main wall along a third edge of the main wall, with the third edge being substantially perpendicular to the first edge and the second edge. The inner end wall is connected to the main wall along a fourth edge of the main end wall, with the fourth edge being substantially perpendicular to the third edge. The outer end wall is further connected to the first and second side walls such that the outer end wall is opposite the inner end wall. The device further includes a means for hingeably connecting the first hollow member to the second hollow member and a means for holding the first hollow member in contact with the second hollow member when the first hollow member is closed around a syringe plunger and barrel.

It is another object of the present invention to provide a syringe assembly, comprising a disposable or nondisposable syringe and a syringe plunger immobilizing device including a first syringe plunger casing member, a second syringe plunger casing member, and a means for connecting the first syringe plunger casing member to the second syringe plunger casing member.

It is a still further object of the present invention to provide a method for immobilizing a syringe, comprising encasing a syringe plunger of a syringe in a syringe plunger immobilizing device. The syringe plunger immobilizing device contains a first syringe plunger casing member, a second syringe plunger casing member, and a means for connecting the first syringe plunger casing member to the second syringe plunger casing member.

It is a still further object of the present invention to provide a method for manufacturing a syringe plunger immobilizing device, comprising filling a mold with a liquid form of a plastic, forming a molded syringe plunger immobilizing device by hardening the liquid form of a plastic, and removing the molded syringe plunger immobilizing device to form the syringe plunger immobilizing device. The present invention also provides a syringe plunger immobilizing device made by this method.

Other features and advantages of the present invention will be come apparent from the following description of the preferred embodiments, which, when taken in conjunction with the accompanying drawings, illustrate the principles of the invention.

DETAILED DESCRIPTION OF THE PREFERRED EMBODIMENTS

Figure 1:
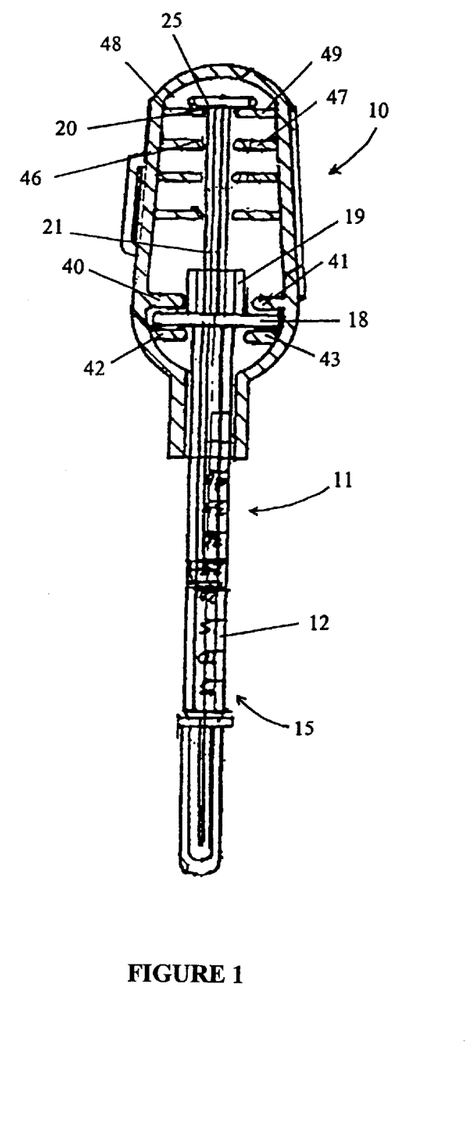
FIG. 1 is a top view of a first embodiment of a syringe plunger immobilizing device according to the present invention, showing the syringe plunger immobilizing device placed on a syringe in an closed position.
Figure 2:
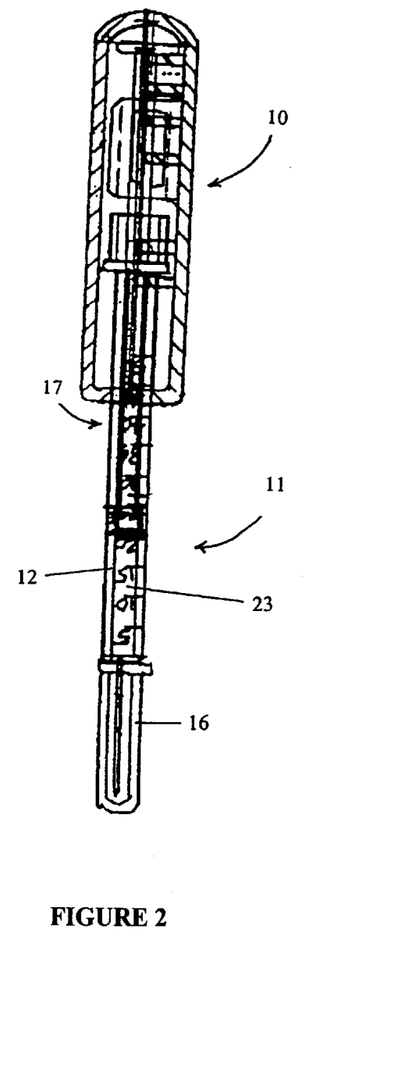
FIG. 2 shows a side view of the same embodiment of a syringe plunger immobilizing device as in FIG. 1, showing the syringe plunger immobilizing device placed on a syringe in an closed position.
Figure 3:
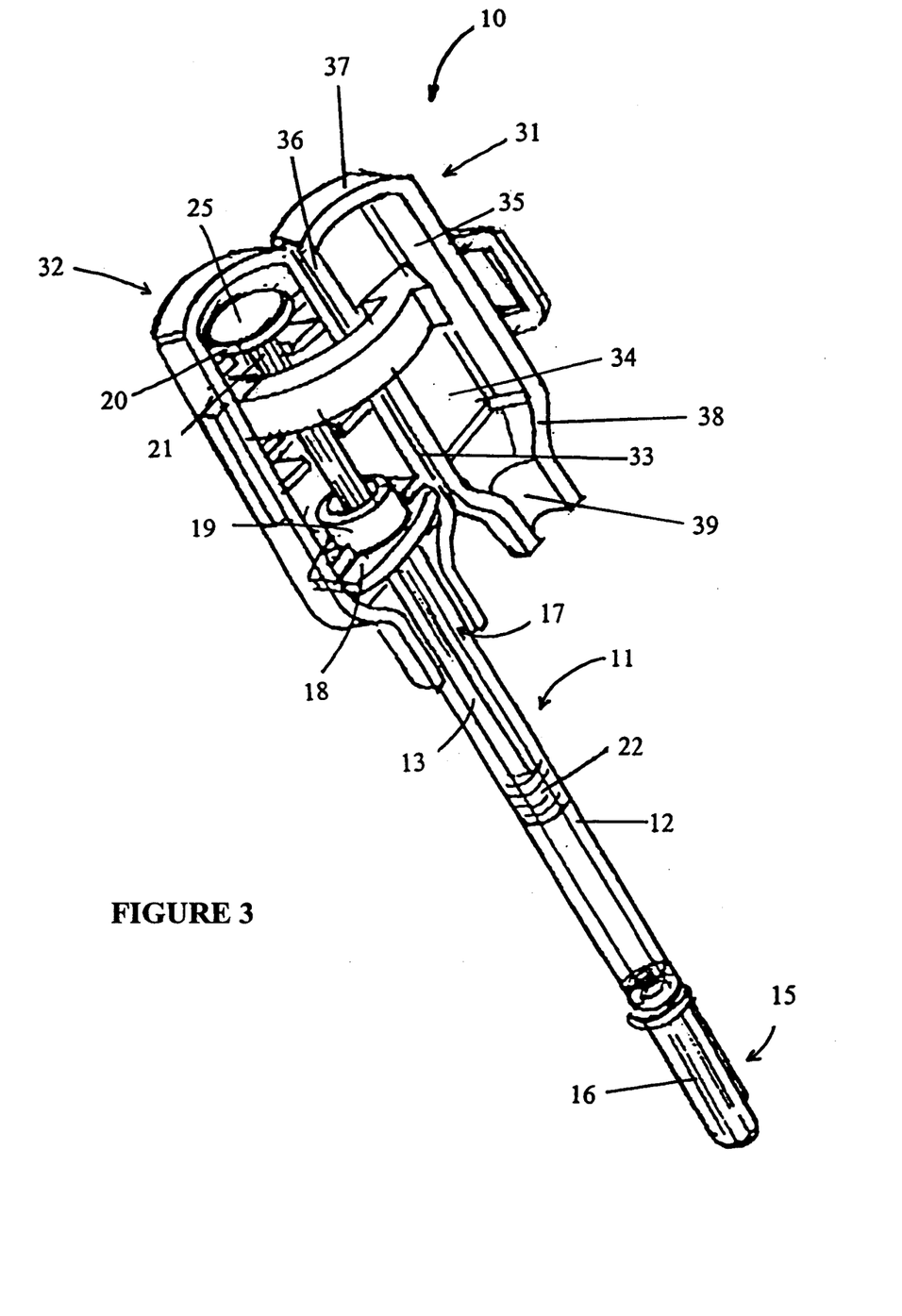
FIG. 3 shows a side view of the same embodiment of a syringe plunger immobilizing device as in FIG. 1, showing the syringe plunger immobilizing device placed on the syringe in an open position.

In accordance with a first embodiment of the invention, a syringe plunger immobilizing device 10 is illustrated in FIGS. 1–3 in engagement with a known medical syringe 11 having a main body element 12 and a plunger element 13 slidably disposed therein. Main body element 12 includes a needle end 15 and an upper end 17. A needle is attached to main body element 12 at needle end 15, and is covered by a protective cover 16. Upper end 17 includes a transverse flange 18 beneath a tubular terminus 19. Plunger element 13 includes a terminus 20, a stem portion 21, and a stopper 22 which penetrates a longitudinal bore 23 in main body element 12. Plunger element 13 includes a transverse cap 25 connected to terminus 20, which under most conditions engages a user's thumb to move plunger element 13 along main body element 12 for injection of a solution. Variations of this type of syringe 11 are well known in the art, and do not form part of the present invention.

Syringe plunger immobilizing device 10 includes a first and a second hollow member 31 and 32, respectively, connected along an edge by a connecting means 33. Each of hollow members 31 and 32 includes a main wall 34, a pair of opposing side walls 35 and 36, and outer end wall 37, and a frusto-conical inner end wall 38 in contact with a cylindrical sleeve portion 39. Each of hollow members 31 and 32 may in addition or in the alternative be shaped so as to follow the contours of syringe 11. Extending from the inner portions of each of hollow members 31 and 32 are first inwardly directed flanges 40 and 41, each of which are adapted to engage an upper surface of transverse flange 18 of syringe 11. Second inwardly directed flanges 42 and 43, in place of or in addition to first inwardly directed flanges 40 and 41, may contact a lower surface of transverse flange 18 to lock main body element 12 substantially in place in one or both of hollow members 31 and 32. Cylindrical sleeve portion 39 is adapted to surround a portion of main body element 12.

In use, syringe 11 is first loaded with any desired solution, such as a solution containing insulin or growth hormone. Thereafter, syringe plunger immobilizing device 10 is placed in contact with syringe 11 such that either or both of first inwardly directed flange 40/41 or second inwardly directed flange 42/43 are in contact with the appropriate surface(s) of transverse flange 18. Thereafter, hollow members 31 and 32 are rotated about connecting means 33 until hollow members 31 and 32 are in contact with one another. Hollow members 31 and 32 are held in contact with one another by any of a number of known means. For example, they may be held in contact with one another through a latching means (as shown in FIGS. 1–3), a hook and loop fastener, or an adhesive element. When hollow members 31 and 32 are held in contact with each other, the upper surface of transverse flange 18 is contacted by both of first inwardly directed flanges 40 and 41. Alternately, both lower surfaces of transverse flange 18 may be contacted by both of second inwardly directed flanges 42 and 43. In a further variation, both surfaces of transverse flange 18 may be contacted by the appropriate inwardly directed flanges, thereby locking main body element 12 in place in the closed syringe plunger immobilizing device 10. In addition, when hollow members 31 and 32 are held in contact with one another, cylindrical sleeve portions 39 of each of hollow members 31 and 32 surround and snugly contact main body element 12. In this closed position, syringe 11 bearing syringe plunger immobilizing device 10 may be easily transported as a single unit.

Connecting means 33 may be in the form of a hinge, a living hinge, a flap, a plurality of rings or tabs, or any other suitable means for connecting first hollow member 31 and second hollow member 32 so that they may rotate about connecting means 33 from an open position to a closed position, and vice versa. As noted above, hollow members 31 and 32 are held in contact with one another by any of a number of known means, including but not limited to a latch, a hook and loop fastener, a living disposable hinge, or an adhesive element. Furthermore, the hollow members 31 and 32 may be held in place by any combination of the above, or by a plurality of one or more of such means. The means are preferably centered around the longitudinal midpoint of the syringe plunger immobilizing device.

Figure 4:
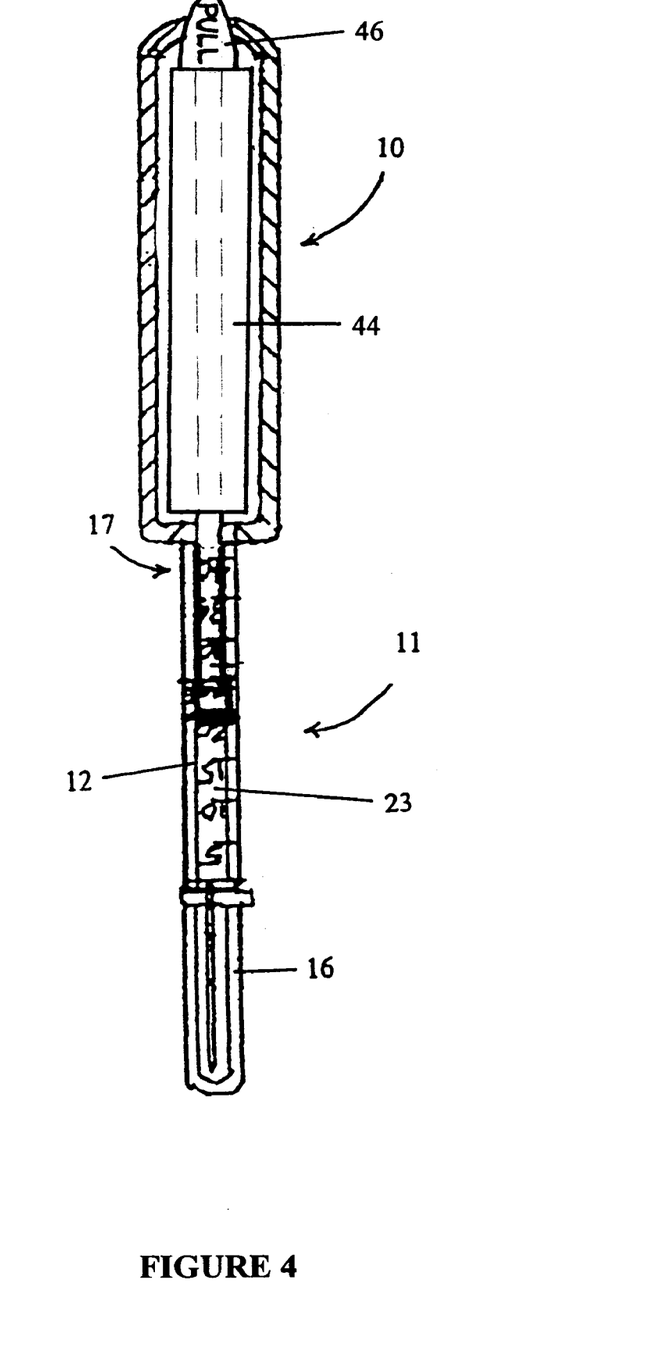
FIG. 4 is a side view of a variation of the first embodiment of a syringe plunger immobilizing device of the present invention, wherein the hingeable connecting means is replaced with a pair of pull-off strips.

In a variation of the first embodiment, shown in FIG. 4, syringe plunger immobilizing device 10 includes a first and a second hollow member 31 and 32, respectively. The structures of first and second hollow members 31 and 32 are as described above, except that they are not connected along an edge by a connecting means 33. Rather, first and second hollow members 31 and 32 are held in contact with one another and with syringe 11 by a pair of pull-off strips 44 and 45 (only pull-off strip 44 is shown in FIG. 4). Pull-off strips 44 and 45 contain an adhesive-bearing surface that contacts the outer surface of first and second hollow members 31 and 32, but do not contact syringe 11. Pull-off strips 44 and 45 each also contain a pull tab 46. In use, pull-off strips 44 and 45 contact each of first and second hollow members 31 and 32 along the longitudinal axis after first and second hollow members 31 and 32 are placed in position on syringe 11. When syringe 11 is to be used, pull tabs 46 on pull-off strips 44 and 45 are pulled in a longitudinal direction along pull-off strips 44 and 45. In doing so, the bond between first and second hollow members 31 and 32 is weakened sufficiently to allow first and second hollow members 31 and 32 to be separated from one another and from syringe 11. Syringe plunger immobilizing device 10 is then removed from syringe 11, permitting the use of syringe 11.

Syringe plunger immobilizing device 10 may be made in several different sizes, as desired. In one embodiment, syringe plunger immobilizing device 10 may be adapted to accommodate various different volumes of solution within syringe 11. In another embodiment, syringe plunger immobilizing device 10 may be adapted to fit various sizes of syringe 11. Syringe 11 commonly is available in sizes having a maximum solution volume of 1 cc, 0.5 cc, or 0.3 cc, and syringe plunger immobilizing device 10 may be adapted to accommodate any of these sizes, or any other size of syringe 11. To accommodate different volumes of solution in the same size of syringe, syringe plunger immobilizing device 10 may vary in longitudinal length, as measured from outer end wall 37 to inner end wall 38. To accommodate different sizes of syringes, syringe plunger immobilizing device 10 may be varied in either or both of longitudinal length or diameter. The 1 cc syringe may have a greater diameter than that of the 0.3 cc syringe, and syringe plunger immobilizing device 10 could be altered in diameter to fit the different syringes. Syringe plunger immobilizing device 10 may be manufactured in a variety of different colors that can be associated with specific sizes or configurations, to aid in easy selection and identification of the desired size. In addition to or in place of various colors, syringe plunger immobilizing device 10 may be manufactured in any other form that assists in identifying the particular size or configuration required by the user, such as, for example, varations in shape, texture, or contour. For example, syringe plunger immobilizing device 10 may bear notations in Braille, to assist visually-impaired users in selecting the proper device or dose. When combined with variations in size and shape of syringe plunger immobilizing device 10, such a device could provide security to the user that the proper syringe/dose combination had been selected.

In a further variation, each of hollow members 31 and 32 could also include third and/or fourth inwardly directed flanges 46/47 and 48–49, respectively. These flanges are located near to outer end wall 37, and engage either or both of an upper and lower surface of transverse cap 20 of plunger element 13. When in a closed position, these flanges, in combination with either or both of inwardly directed flanges 40/41 and 42/43, lock plunger element 13 in place with respect to main body element 12, allowing substantially no movement of plunger element 13 within the bore of main body element 12. A series of such inwardly directed flanges, as shown in FIG. 1, could optionally be included inside hollow members 31 and 32 to lock plunger element 13 in a preferred position with respect to main body element 12. In this manner, any of a number of different doses of the medicament could be held in syringe 11 and the plunger secured in place within syringe plunger immobilizing device 10.

Where hollow members 31 and 32 are shaped so as to follow the contours of syringe 11 between tubular terminus 19 and transverse cap 25, then third and/or fourth inwardly directed flanges 46/47 and 48–49 need not be incorporated into hollow members 31 and 32. In this instance, the lengths of hollow members 31 and 32 may be varied, as required, to accommodate different volumes of medicament or other solution held in preloaded syringe 11. For example, a syringe holding a volume of 1 cc would require a syringe plunger immobilizing device 10 of greater length than the same size of syringe holding a volume of 0.3 cc. However, third and/or fourth inwardly directed flanges 46/47 and 48–49 may still be incorporated into hollow members 31 and 32, if desirable.

Syringe plunger immobilizing device 10 may be made of any desired material, including but not limited to a plastic, wood, a composite material, metal, or any combination of these. Preferably, syringe plunger immobilizing device 10 is made of plastic. Some of the plastics suitable for use in the invention include, for example, polypropylene, polyethylene, polystyrene, polyvinylchloride, and the like. In this case, where syringe plunger immobilizing device 10 is made of a plastic material, it may be manufactured by any appropriate method generally known to those in the art, including but not limited to injection molding, extrusion, and thermoforming. Preferably, syringe plunger immobilizing device 10 is manufactured by injection molding.

Examples of composite materials suitable for use in the present invention include glass fiber reinforced composites, such as fiberglas, and carbon fiber reinforced organic composites.

Figure 5:
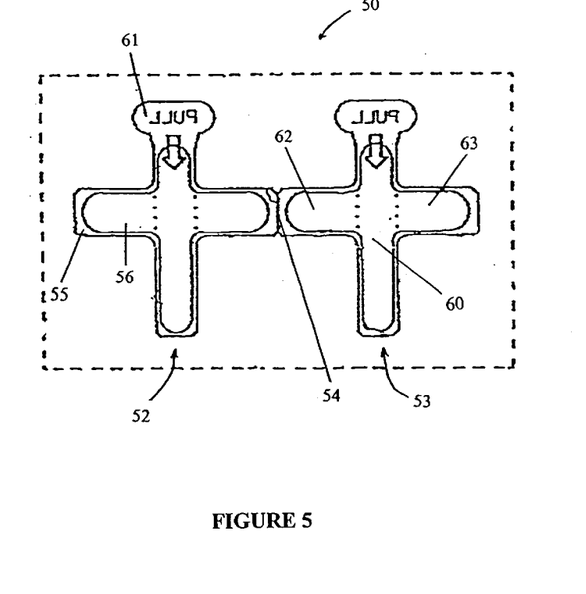
FIG. 5 is a side view of a second embodiment of a syringe plunger immobilizing device according to the present invention.
Figure 6:
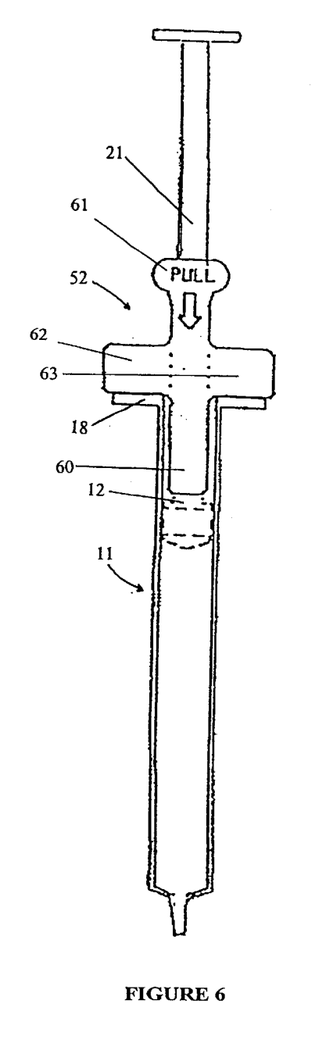
FIG. 6 is a side view of the second embodiment of a syringe plunger immobilizing device as in FIG. 5, showing the syringe plunger immobilizing device placed onto a syringe.

A second embodiment of the present invention is illustrated in FIGS. 5 and 6. A preferably transparent or translucent syringe plunger immobilizing strip 50 includes first planar element 52 and second planar element 53 connected at a fold line 54. First planar element 52 and second planar element 53 are substantially similar or identical, and may be mirror images of one another. Each of first planar element 52 and second planar element 53 includes a substantially cruciform-shaped base 55 and a laminated foam adhesive member 56. Each also includes a longitudinally-extending portion 60, as well as first and second laterally-extending members 62 and 63, extending in opposite directions from longitudinally extending portion 60. First and second laterally-extending members 62 and 63 and longitudinally-extending portion 60 have an adhesive-bearing surface, and an adhesive-free pull tab 61 at one end of longitudinally extending portion 60. A series of longitudinally-extending perforations or the like define the boundary between longitudinally-extending portion 60 and each of first and second laterally extending members 62 and 63. Syringe plunger immobilizing strip 50 may be made of a metal, such as, for example, heavy gauge aluminum foil, cloth, or plastic. Although adhesive-free pull tab 61 is shown at one end of longitudinally-extending portion 60, it may be at the other end, or adhesive-free pull tab 61 may be mounted on both ends of longitudinally-extending portion 60, as desired.

In use, syringe plunger immobilizing strip 50 is removed from its sterile enclosure, if present, and attached to a preloaded syringe 11 as shown in FIG. 6. Essentially, syringe plunger immobilizing strip 50 is folded about the fold line and placed on preloaded syringe 11, with laminated foam adhesive member 56 of each of first planar element 52 and second planar element 53 attaching to main body element 12 and plunger stem portion 21 via the adhesive-bearing surface of longitudinally-extending portion 60. Thereafter, first and second laterally-extending members 62 and 63 of first planar element 52 may be adhered to the opposing laterally extending members 62 and 63 of second planar member 53. In the alternative, first and second laterally-extending members 62 and 63 of each of first and second planar members 52 and 53 may be adhered to a surface of transverse flange 18. For injection, pull tabs 61 of first and second planar elements 52 and 53 are pulled in the direction of longitudinally-extending portions 60 through the perforations so that movement of plunger 13 relative to main body element 12 is enabled. Syringe 11 may then be used in the normal manner.

Figure 7:
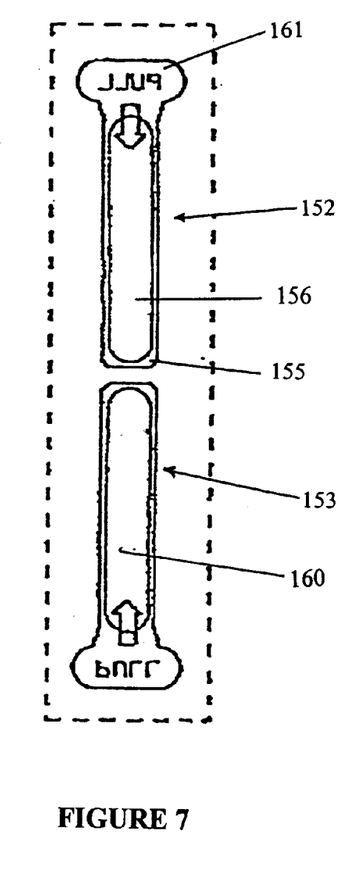
FIG. 7 is a side view of a third embodiment of a syringe plunger immobilizing device according to the present invention.
Figure 8:
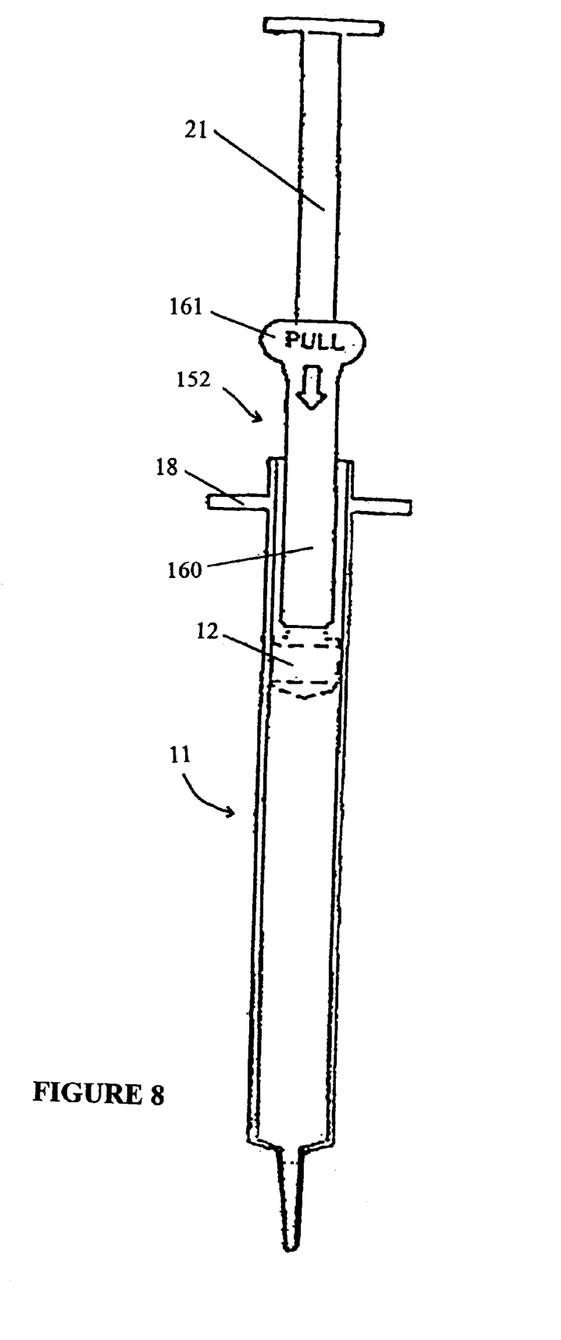
FIG. 8 is a side view of the third embodiment of a syringe plunger immobilizing device as in FIG. 7, showing the syringe plunger immobilizing device placed onto a syringe.

A third embodiment of the present invention is shown in FIGS. 7 and 8. This embodiment is a variation of the second embodiment, and therefore parts corresponding to those of the second embodiment have been designated with the same reference numerals, except that such reference numerals are preceded by a prefix "1". The third embodiment differs from the second embodiment in the elimination of fold line and also the laterally-extending members 62 and 63. Each of first and second planar elements 152 and 153 may be separately applied, and need not contact one another. Each of first and second planar elements 152 and 153 includes a longitudinally-extending base 155 and a laminated foam adhesive member 156. Laminated foam adhesive member 156 includes a longitudinally extending member 160, with an adhesive pull tab 161 at one end of longitudinally extending member 160. In use, one or both of first and second planar elements 152 and 153 are removed from the sterile enclosure, if present, and laminated foam adhesive member 156 is attached to preloaded syringe 11 via an adhesive-bearing surface of longitudinally-extending member 160. For injection, adhesive pull tab 160 is pulled in the direction of longitudinally-extending member so that movement of plunger 13 relative to main body element 12 of syringe 11 is enabled. Syringe 11 may then be used in the normal manner.

The embodiments of the present invention are particularly suitable for use by persons who must frequently self-inject medications, such as, for example, diabetics, who must often inject insulin; children who suffer from a deficiency of growth hormone and who must therefore receive frequent growth hormone injections; and persons who have severe allergic reactions to common allergens. In addition, the embodiments of the present invention may also be useful to any person who requires a convenient device that would allow the user to prefill syringes with a desired volume of a medicine or other solution and after use, discard the used syringe without the need to retain anything associated with the injection. Thus, the device of the invention might be used by animal health personnel, emergency medical personnel, biomedical research personnel, and the like. The device of the present invention is particularly advantageous for those who wish to transport such preloaded syringes, since it avoids the need to carry the medicine or other solution in a separate container and load the syringe just before use.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. Throughout this application various publications and patents are cited. The contents of these publications and patents are hereby incorporated by reference into the present application.

What is claimed is:

1. A syringe plunger immobilizing device, comprising:
   a first hollow member;
   a second hollow member;
   a means for hingeably connecting said first hollow member to said second hollow member; and
   a means for holding said first hollow member in contact with said second hollow membered;
   wherein each of said first hollow member and said second hollow member includes a main wall, a first side wall, a second side wall, an outer end wall, a frusto-conical inner end wall and a cylindrical sleeve portion;
   said first side wall being connected to said main wall along a first edge of said main wall, and said second side wall being connected to said main wall along a second edge substantially parallel to said first edge such that said first side wall is opposite said second side wall;
   said outer end wall being connected to said main wall along a third edge of said main wall, said third edge being substantially perpendicular to said first edge and said second edge;
   said inner end wall being connected to said main wall along a fourth edge of said main end wall, said fourth edge being substantially perpendicular to said third edge;
   said outer end wall further being connected to said first side wall and said second side wall such that said outer end wall is opposite said inner end wall; and
   said cylindrical sleeve portion contacting said inner end wall.

2. The syringe plunger immobilizing device of claim 1, wherein each of said first hollow member and said second hollow member has an inwardly directed flange, said flange being effective to contact a surface of a finger-engaging transverse flange of a syringe.

3. The syringe plunger immobilizing device of claim 1, wherein said means for hingeably connecting said first hollow member to said second hollow member is a member selected from the group consisting of a hinge, a flap, a plurality of rings, and a plurality of tabs.

4. The syringe plunger immobilizing device of claim 1, wherein said means for holding said first hollow member in contact with said second hollow member is a member selected from the group consisting of a latch, an adhesive element, or a hook and loop fastener.

5. The syringe plunger immobilizing device of claim 2, wherein each of said first hollow member and said second hollow member includes an additional inwardly directed flange, said additional inwardly directed flange being effective to engage a surface of a transverse cap said of a syringe plunger.

6. The syringe plunger immobilizing device of claim 2, wherein each of said first hollow member and said second hollow member includes a plurality of additional inwardly directed flanges, each of said plurality of additional inwardly directed flanges being effective to engage a surface of a transverse cap said of a syringe plunger.

7. A disposable syringe assembly, comprising:
   a disposable syringe; and
   a disposable syringe plunger immobilizing device;
   said disposable syringe plunger immobilizing device including a first syringe plunger casing member; a second syringe plunger casing member; a means for connecting said first syringe plunger casing member to said second syringe plunger casing member, and a means for holding said first hollow member in contact with said second hollow member;
   wherein each of said first hollow member and said second hollow member includes a main wall, a first side wall, a second side wall, an outer wall, an outer end wall, a frusto-conical inner end wall and a cylindrical sleeve portion;
   said first side wall being connected to said main wall along a first edge of said main wall, and said second side wall being connected to said main wall along a second edge substantially parallel to said first edge such that said first side wall is opposite said second wall;
   said outer end wall being connected to said main wall along a third edge of said main wall, said third edge being substantially perpendicular to said first edge and said second edge;
   said inner end wall being connected to said main wall along a fourth edge of said main end wall, said fourth edge being substantially perpendicular to said third edge;
   said outer end wall further being connected to said first side wall and said second side wall such that said outer end wall is opposite said inner end wall; and
   said cylindrical sleeve portion contacting said inner end wall.

8. The syringe plunger immobilizing device of claim 7, wherein each of said first hollow member and said second hollow member has an inwardly directed flange, said flange being effective to contact a surface of a finger-engaging transverse flange of a syringe.

9. The syringe plunger immobilizing device of claim 7, wherein said means for hingeably connecting said first hollow member to said second hollow member is a member selected from the group consisting of a hinge, a flap, a plurality of rings, and a plurality of tabs.

10. The syringe plunger immobilizing device of claim 7, wherein said means for holding said first hollow member in contact with said second hollow member is a member selected from the group consisting of a latch, an adhesive element, or a hook and loop fastener.

11. The syringe plunger immobilizing device of claim 8, wherein each of said first hollow member and said second hollow member includes an additional inwardly directed flange, said additional inwardly directed flange being effective to engage a surface of a transverse cap said of a syringe plunger.

12. The syringe plunger immobilizing device of claim 8, wherein each of said first hollow member and said second hollow member includes a plurality of additional inwardly directed flanges, each of said plurality of additional inwardly directed flanges being effective to engage a surface of a transverse cap said of a syringe plunger.

13. A method for immobilizing a syringe, comprising the steps of:

contacting a syringe plunger of a syringe with a syringe plunger immobilizing device;

said syringe plunger immobilizing device containing a first syringe plunger casing member;

a second syringe plunger casing member; a means for connecting said first syringe plunger casing member to said second syringe plunger casing member, and a means for holding said first hollow member in contact with said second hollow member;

wherein said first and second syringe plunger casing members are adapted to allow substantially no movement between said syringe plunger and said syringe, and engage a traverse flange in said syringe.

14. A syringe plunger immobilizing device, comprising:

a first hollow member;

a second hollow member;

a pair of opposing pull-off strips for connecting said first hollow member to said second hollow member; and a means for holding said first hollow member in contact with said second hollow member;

wherein each of said first hollow member and said second hollow member includes a main wall, a first side wall, a second side wall, an outer end wall, a frusto-conical inner end wall and a cylindrical sleeve portion;

said first side wall being connected to said main wall along a first edge of said main wall, and said second side wall being connected to said main wall along a second edge substantially parallel to said first edge such that said first side wall is opposite said second side wall;

said outer end wall being connected to said main wall along a third edge of said main wall, said third edge being substantially perpendicular to said first edge and said second edge;

said inner end wall being connected to said main wall along a fourth edge of said main end wall, said fourth edge being substantially perpendicular to said third edge;

said outer end w all further being connected to said first side wall and said second side wall such that said outer end wall is opposite said inner end wall;

and said cylindrical sleeve portion contacting said inner end wall.

15. A disposable syringe assembly, comprising:

a disposable syringe; and a disposable syringe plunger immobilizing device;

said disposable syringe plunger immobilizing device including a first syringe plunger casing member;

a second syringe plunger casing member; a pair of opposing pull-off strips for connecting said first syringe plunger casing member to said second syringe plunger casing member, and a means for holding said first hollow member in contact with said second hollow members;

wherein each of said first hollow member and said second hollow member includes a main wall, a first side wall, a second side wall, an outer end wall, a frusto-conical inner end wall and a cylindrical sleeve portion;

said first side wall being connected to said main wall along a first edge of said main wall, and said second side wall being connected to said main wall along a second edge substantially parallel to said first edge such that said first side wall is opposite said second side wall;

said outer end wall being connected to said main wall along a third edge of said main wall, said third edge being substantially perpendicular to said first edge and said second edge;

said inner end wall being connected to said main wall along a fourth edge of said main end wall, said fourth edge being substantially perpendicular to said third edge;

said outer end wall further being connected to said first side wall and said second side wall such that said outer end wall is opposite said inner end wall; and said cylindrical sleeve portion contacting said inner end wall.

* * * * *